US010967084B2

(12) United States Patent
Fryer

(10) Patent No.: US 10,967,084 B2
(45) Date of Patent: Apr. 6, 2021

(54) FLOW RESTRICTOR

(71) Applicant: ASP Global Manufacturing GmbH, Schaffhausen (CH)

(72) Inventor: Ben Fryer, Lake Forest, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 340 days.

(21) Appl. No.: 15/844,237

(22) Filed: Dec. 15, 2017

(65) Prior Publication Data

US 2019/0184048 A1 Jun. 20, 2019

(51) Int. Cl.
*A61B 90/70* (2016.01)
*A61L 2/20* (2006.01)
*A61B 1/12* (2006.01)

(52) U.S. Cl.
CPC .............. *A61L 2/208* (2013.01); *A61B 90/70* (2016.02); *A61B 1/121* (2013.01); *A61B 2090/701* (2016.02); *A61L 2202/122* (2013.01); *A61L 2202/123* (2013.01); *A61L 2202/14* (2013.01); *A61L 2202/15* (2013.01); *A61L 2202/24* (2013.01)

(58) Field of Classification Search
CPC ................................................ A61B 2090/701
See application file for complete search history.

(56) References Cited

U.S. PATENT DOCUMENTS

| 3,701,434 A | 10/1972 | Moore |
| 4,416,417 A | 11/1983 | Sanderson et al. |
| 4,637,378 A | 1/1987 | Sasa |
| 4,748,003 A | 5/1988 | Riley |
| 4,798,292 A | 1/1989 | Hauze |
| 4,878,484 A | 11/1989 | Miyagi |
| 4,943,414 A | 7/1990 | Jacobs et al. |
| 5,084,239 A | 1/1992 | Moulton et al. |
| 5,165,503 A | 11/1992 | Hoffman |
| 5,279,317 A | 1/1994 | Bowman et al. |
| 5,288,467 A | 2/1994 | Biermaier |
| 5,308,406 A | 5/1994 | Wallock et al. |
| 5,320,119 A | 6/1994 | Griffiths |
| 5,348,711 A | 9/1994 | Johnson et al. |

(Continued)

FOREIGN PATENT DOCUMENTS

| AU | 198820053 A | 2/1989 |
| AU | 622412 B2 | 4/1992 |

(Continued)

OTHER PUBLICATIONS

PCT International Search Report (ISR) for International Application No. PCT/IB2019/055216 dated Oct. 31, 2019.

(Continued)

*Primary Examiner* — Donald R Spamer
(74) *Attorney, Agent, or Firm* — Etan S. Chatlynne; Roberts Calderon Safran & Cole P.C.

(57) ABSTRACT

An apparatus that assists in sterilizing an endoscope inside a sterilizer employing a gaseous sterilant, e.g., hydrogen peroxide, is disclosed. The apparatus may include a dry booster and a flow restrictor that includes two tubes, which may be connected to channels of an endoscope and the dry booster. The flow restrictor may be used to change the flow rates through the channels to assist in delivering sterilant throughout the channels.

10 Claims, 4 Drawing Sheets

(56) References Cited

U.S. PATENT DOCUMENTS

| | | | |
|---|---|---|---|
| 5,413,758 A | 5/1995 | Caputo et al. |
| 5,471,706 A | 12/1995 | Wallock et al. |
| 5,490,975 A | 2/1996 | Dane |
| 5,492,672 A | 2/1996 | Childers et al. |
| 5,511,568 A | 4/1996 | Bowman et al. |
| 5,533,518 A | 7/1996 | Vogler |
| 5,547,456 A | 8/1996 | Strobl et al. |
| 5,551,462 A | 9/1996 | Biermaier |
| 5,556,607 A | 9/1996 | Childers et al. |
| 5,580,530 A | 12/1996 | Kowatsch et al. |
| 5,634,880 A | 6/1997 | Feldman et al. |
| 5,645,796 A | 7/1997 | Caputo et al. |
| 5,667,495 A | 9/1997 | Bitdinger et al. |
| 5,733,503 A | 3/1998 | Kowatsch et al. |
| 5,807,238 A | 9/1998 | Feldman et al. |
| 5,868,667 A | 2/1999 | Lin et al. |
| 5,906,802 A | 5/1999 | Langford |
| 5,961,921 A | 10/1999 | Addy et al. |
| 5,961,937 A | 10/1999 | Gobbato |
| 5,980,825 A | 11/1999 | Addy et al. |
| 6,030,579 A | 2/2000 | Addy et al. |
| 6,068,817 A | 5/2000 | Addy et al. |
| 6,083,458 A | 7/2000 | Lin et al. |
| 6,099,812 A | 8/2000 | Allen et al. |
| 6,132,680 A | 10/2000 | Addy et al. |
| 6,162,395 A | 12/2000 | Kowanko |
| 6,174,502 B1 | 1/2001 | Addy et al. |
| 6,187,265 B1 | 2/2001 | Wu et al. |
| 6,193,932 B1 | 2/2001 | Wu et al. |
| 6,264,902 B1 | 7/2001 | Howlett |
| 6,312,646 B2 | 11/2001 | Kowanko |
| 6,319,480 B1 | 11/2001 | Addy et al. |
| 6,325,972 B1 | 12/2001 | Jacobs et al. |
| 6,365,103 B1 | 4/2002 | Fournier |
| 6,379,631 B1 | 4/2002 | Wu |
| 6,451,255 B1 * | 9/2002 | Williams ............... A61L 2/186 422/28 |
| 6,495,100 B1 | 12/2002 | Lin et al. |
| 6,528,017 B2 | 3/2003 | Jacobs et al. |
| 6,534,002 B1 | 3/2003 | Lin et al. |
| 6,569,128 B1 * | 5/2003 | Christensen ...... A61M 5/16804 604/246 |
| 6,572,819 B1 | 6/2003 | Wu et al. |
| 6,589,481 B1 | 7/2003 | Lin et al. |
| 6,627,150 B1 | 9/2003 | Wang et al. |
| 6,656,426 B1 | 12/2003 | Wang et al. |
| 6,692,693 B2 | 2/2004 | Wu |
| 6,977,061 B2 | 12/2005 | Lin et al. |
| 7,132,089 B2 | 11/2006 | Lacabanne |
| 7,179,419 B2 | 2/2007 | Lin et al. |
| 7,229,591 B2 | 6/2007 | Wu et al. |
| 7,252,800 B2 | 8/2007 | Jacobs et al. |
| 7,285,254 B2 | 10/2007 | Lin et al. |
| 7,294,305 B2 | 11/2007 | Lin et al. |
| 7,300,638 B2 | 11/2007 | Williams et al. |
| 7,468,159 B2 | 12/2008 | Lin et al. |
| 7,569,180 B2 | 8/2009 | Kohler et al. |
| 7,670,550 B2 | 3/2010 | Lin et al. |
| 7,803,316 B2 | 9/2010 | Lin et al. |
| 7,862,769 B2 | 1/2011 | Kaiser |
| 7,993,602 B2 | 8/2011 | Moriyama et al. |
| 8,118,042 B2 | 2/2012 | Ngo et al. |
| 8,298,494 B2 | 10/2012 | Komiya et al. |
| 8,444,930 B2 | 5/2013 | Komiya et al. |
| 8,444,940 B2 | 5/2013 | Komiya et al. |
| 8,460,176 B2 | 6/2013 | McGrath |
| 8,658,092 B2 | 2/2014 | Kohler et al. |
| 8,840,836 B2 | 9/2014 | Olson |
| 8,926,501 B2 | 1/2015 | Powell et al. |
| 9,060,804 B2 | 6/2015 | Meyer |
| 9,132,456 B2 | 9/2015 | Kawai et al. |
| 9,144,469 B1 | 9/2015 | Geddis et al. |
| 9,216,074 B2 | 12/2015 | Vedovelli |
| 9,295,374 B2 | 3/2016 | Metras |
| 9,533,136 B2 | 1/2017 | Midgette et al. |
| 9,922,533 B2 | 3/2018 | Hayes et al. |
| 2001/0000227 A1 | 4/2001 | Kowanko |
| 2001/0036422 A1 | 11/2001 | Lin et al. |
| 2002/0015673 A1 | 2/2002 | Moriyama |
| 2002/0191938 A1 | 12/2002 | Sheetz et al. |
| 2003/0026729 A1 | 2/2003 | Wu et al. |
| 2004/0105780 A1 | 6/2004 | Lin et al. |
| 2004/0118440 A1 | 6/2004 | Sasaki et al. |
| 2005/0000553 A1 | 1/2005 | Noguchi et al. |
| 2005/0191208 A1 | 9/2005 | Lin et al. |
| 2005/0191209 A1 | 9/2005 | Lin et al. |
| 2005/0191222 A1 | 9/2005 | Lin et al. |
| 2005/0216029 A1 * | 9/2005 | Gingrich ............... A61B 10/06 606/108 |
| 2005/0260097 A1 | 11/2005 | Williams et al. |
| 2006/0263245 A1 | 11/2006 | Watanabe et al. |
| 2007/0258873 A1 | 11/2007 | Wu et al. |
| 2008/0131342 A1 | 6/2008 | Wu et al. |
| 2009/0107529 A1 | 4/2009 | Lin et al. |
| 2009/0225517 A1 | 9/2009 | Nelson et al. |
| 2009/0324445 A1 | 12/2009 | Kohler et al. |
| 2012/0031506 A1 | 2/2012 | Komiya et al. |
| 2012/0275954 A1 | 11/2012 | Olson |
| 2013/0000746 A1 | 1/2013 | Komiya et al. |
| 2013/0098400 A1 * | 4/2013 | Nguyen ............... A61B 1/125 134/18 |
| 2013/0156640 A1 | 6/2013 | Kohler et al. |
| 2015/0073214 A1 | 3/2015 | Ueda |
| 2015/0359599 A1 | 12/2015 | Fagan et al. |
| 2015/0374868 A1 | 12/2015 | Bruce et al. |
| 2017/0007731 A1 | 1/2017 | Sharma |
| 2017/0210504 A1 | 7/2017 | Aguirre |
| 2017/0224434 A1 | 8/2017 | Schwatzbauer et al. |
| 2017/0224859 A1 | 8/2017 | Broninx et al. |
| 2019/0046024 A1 | 2/2019 | Morrison |
| 2019/0175775 A1 | 6/2019 | Fryer et al. |
| 2019/0201568 A1 | 7/2019 | Rhodes |
| 2019/0388672 A1 | 12/2019 | McNeal et al. |

FOREIGN PATENT DOCUMENTS

| | | |
|---|---|---|
| AU | 4673796 | 1/1997 |
| AU | 1744097 A | 7/1997 |
| AU | 1770197 A | 10/1997 |
| AU | 2454997 A | 10/1997 |
| AU | 700172 B2 | 12/1998 |
| AU | 9710398 A | 7/1999 |
| AU | 720169 B2 | 5/2000 |
| AU | 721001 B2 | 6/2000 |
| AU | 6556399 A | 7/2000 |
| AU | 723034 B2 | 8/2000 |
| AU | 733363 B2 | 5/2001 |
| AU | 7241900 A | 6/2001 |
| AU | 200072377 A1 | 6/2001 |
| AU | 3352301 A | 8/2001 |
| AU | 200118028 A | 6/2002 |
| AU | 755860 B2 | 1/2003 |
| AU | 755983 B2 | 1/2003 |
| AU | 766746 B2 | 10/2003 |
| AU | 769624 B2 | 1/2004 |
| AU | 771288 B2 | 3/2004 |
| AU | 755983 C | 7/2004 |
| AU | 2001233523 B2 | 9/2004 |
| AU | 2005249347 B2 | 12/2005 |
| AU | 2005227377 A1 | 4/2006 |
| AU | 2005227377 B2 | 6/2010 |
| BR | 8803795 A | 2/1989 |
| BR | 9602186 A | 4/1998 |
| BR | 9708498 A | 8/1999 |
| BR | 9805358 A | 11/1999 |
| BR | PI0504322 A | 6/2006 |
| BR | 9602186 B1 | 2/2010 |
| CA | 1321702 C | 8/1993 |
| CA | 2256040 A1 | 6/1999 |
| CA | 2050368 C | 3/2000 |
| CA | 2293199 A1 | 6/2000 |
| CA | 2357838 A1 | 7/2000 |
| CA | 2357843 A1 | 7/2000 |
| CA | 2329208 A1 | 6/2001 |

(56) References Cited

FOREIGN PATENT DOCUMENTS

| | | |
|---|---|---|
| CA | 2329385 A1 | 6/2001 |
| CA | 2298165 A1 | 8/2001 |
| CA | 2251153 C | 6/2005 |
| CA | 2241318 C | 9/2005 |
| CA | 2201572 C | 11/2005 |
| CA | 2566580 A1 | 12/2005 |
| CA | 2522509 A1 | 4/2006 |
| CA | 2298165 C | 5/2006 |
| CA | 2175867 C | 8/2006 |
| CA | 2221149 C | 10/2006 |
| CA | 2293199 C | 10/2006 |
| CA | 2329208 C | 12/2006 |
| CA | 2329385 C | 4/2007 |
| CA | 2357843 C | 4/2007 |
| CA | 2256040 C | 2/2008 |
| CA | 2566580 C | 2/2010 |
| CA | 2357838 C | 6/2010 |
| CA | 2522509 C | 5/2014 |
| CH | 688083 A5 | 5/1997 |
| CN | 1169877 A | 1/1998 |
| CN | 1223148 A | 7/1999 |
| CN | 1112938 C | 7/2003 |
| CN | 1765420 A | 5/2006 |
| CN | 1997407 A | 7/2007 |
| CN | 100371025 C | 2/2008 |
| CN | 101121025 A | 2/2008 |
| CN | 100496616 C | 6/2009 |
| CN | 1997407 B | 11/2010 |
| CN | 101121025 B | 1/2012 |
| CN | 102481092 A | 5/2012 |
| CN | 102871640 A | 1/2013 |
| CN | 102481092 B | 4/2014 |
| DE | 3819257 C1 | 7/1989 |
| DE | 3874837 T2 | 4/1993 |
| DE | 4404460 C1 | 6/1995 |
| DE | 69120174 T2 | 11/1996 |
| DE | 19858391 A1 | 7/1999 |
| DE | 69605548 T2 | 7/2000 |
| DE | 69626697 T2 | 1/2004 |
| DE | 69724958 T2 | 7/2004 |
| DE | 69726329 T2 | 11/2004 |
| DE | 69631561 T2 | 12/2004 |
| DE | 60019538 T2 | 5/2005 |
| DE | 69923758 T2 | 4/2006 |
| DE | 69635595 T2 | 8/2006 |
| DE | 69931280 T2 | 5/2007 |
| DE | 69933137 T2 | 8/2007 |
| DE | 69839085 T2 | 1/2009 |
| DE | 69931280 T3 | 1/2010 |
| DE | 19858391 B4 | 9/2012 |
| DK | 0799621 T3 | 3/2004 |
| EP | 0 212 426 B1 | 3/1987 |
| EP | 0302419 A2 | 2/1989 |
| EP | 345713 A2 | 12/1989 |
| EP | 0302419 A3 | 5/1990 |
| EP | 0345713 A3 | 7/1991 |
| EP | 0474137 A2 | 3/1992 |
| EP | 0474137 A3 | 8/1992 |
| EP | 0302419 B1 | 9/1992 |
| EP | 583465 A1 | 2/1994 |
| EP | 0345713 B1 | 9/1994 |
| EP | 0474137 B1 | 6/1996 |
| EP | 0742017 A2 | 11/1996 |
| EP | 0799621 A1 | 10/1997 |
| EP | 0742017 A3 | 1/1998 |
| EP | 0833704 A1 | 4/1998 |
| EP | 0907381 A1 | 4/1999 |
| EP | 0923949 A2 | 6/1999 |
| EP | 0928205 A1 | 7/1999 |
| EP | 0833704 B1 | 12/1999 |
| EP | 1016371 A1 | 7/2000 |
| EP | 0923949 A3 | 3/2001 |
| EP | 1110557 A2 | 6/2001 |
| EP | 1110558 A2 | 6/2001 |
| EP | 1140220 A1 | 10/2001 |
| EP | 1146915 A1 | 10/2001 |
| EP | 1257302 A1 | 11/2002 |
| EP | 0928205 B1 | 3/2003 |
| EP | 1110557 A3 | 4/2003 |
| EP | 1110558 A3 | 4/2003 |
| EP | 0907381 B1 | 9/2003 |
| EP | 0799621 B1 | 11/2003 |
| EP | 1380309 A1 | 1/2004 |
| EP | 0742017 B1 | 2/2004 |
| EP | 1016371 B1 | 2/2005 |
| EP | 1110558 B1 | 4/2005 |
| EP | 1552853 A2 | 7/2005 |
| EP | 1380309 B1 | 12/2005 |
| EP | 1647285 A1 | 4/2006 |
| EP | 1146915 B1 | 5/2006 |
| EP | 1140220 B1 | 9/2006 |
| EP | 1747027 A2 | 1/2007 |
| EP | 0923949 B1 | 2/2008 |
| EP | 1552853 A3 | 2/2008 |
| EP | 1908483 A2 | 4/2008 |
| EP | 1908483 A3 | 7/2008 |
| EP | 1110557 B1 | 3/2009 |
| EP | 1747027 A4 | 4/2009 |
| EP | 1146915 B2 | 9/2009 |
| EP | 2 138 127 A1 | 12/2009 |
| EP | 1 757 313 B1 | 3/2011 |
| EP | 1908483 B1 | 10/2012 |
| EP | 2572628 A1 | 3/2013 |
| EP | 2 614 840 A2 | 7/2013 |
| EP | 2572628 A4 | 7/2013 |
| EP | 1647285 B1 | 11/2013 |
| EP | 1747027 B1 | 1/2014 |
| EP | 2572628 B1 | 6/2014 |
| EP | 2786695 A1 | 10/2014 |
| ES | 2035189 T3 | 4/1993 |
| ES | 2059622 T3 | 11/1994 |
| ES | 2141472 T3 | 3/2000 |
| ES | 2206703 T3 | 5/2004 |
| ES | 2210455 T3 | 7/2004 |
| ES | 2213766 T3 | 9/2004 |
| ES | 2237894 T3 | 8/2005 |
| ES | 2238025 T3 | 8/2005 |
| ES | 2254864 T3 | 6/2006 |
| ES | 2263296 T3 | 12/2006 |
| ES | 2273518 T3 | 5/2007 |
| ES | 2300118 T3 | 6/2008 |
| ES | 2321580 T3 | 6/2009 |
| ES | 2263296 T5 | 12/2009 |
| ES | 2395962 T3 | 2/2013 |
| ES | 2447769 T3 | 3/2014 |
| ES | 2454549 T3 | 4/2014 |
| IE | 882341 L | 1/1989 |
| IE | 63435 B1 | 4/1995 |
| IN | 199802163 I2 | 3/2005 |
| IN | 225363 B | 9/2007 |
| IN | 200601331 P3 | 9/2007 |
| JP | S58-180130 A | 10/1983 |
| JP | S6449563 A | 2/1989 |
| JP | H05317390 A | 12/1993 |
| JP | H09609 A | 1/1997 |
| JP | H1028722 A | 2/1998 |
| JP | H11244362 A | 9/1999 |
| JP | H11253537 A | 9/1999 |
| JP | 2000102508 A | 4/2000 |
| JP | 2000217892 A | 8/2000 |
| JP | 2001-204799 A | 7/2001 |
| JP | 2001309966 A | 11/2001 |
| JP | 2004073259 A | 3/2004 |
| JP | 2004-167262 A | 6/2004 |
| JP | 2005-52410 A | 3/2005 |
| JP | 2005-205227 A | 8/2005 |
| JP | 2006-055325 A | 3/2006 |
| JP | 2006110349 A | 4/2006 |
| JP | 2006305379 A | 11/2006 |
| JP | 2007236965 A | 9/2007 |
| JP | 4153029 B2 | 9/2008 |
| JP | 4212743 B2 | 1/2009 |
| JP | 4303299 B2 | 7/2009 |
| JP | 4330664 B2 | 9/2009 |

(56) References Cited

FOREIGN PATENT DOCUMENTS

| | | |
|---|---|---|
| JP | 4459432 B2 | 4/2010 |
| JP | 4535293 B2 | 9/2010 |
| JP | 4722660 B2 | 7/2011 |
| JP | 2012-040240 A | 3/2012 |
| JP | 4892111 B1 | 3/2012 |
| JP | 4892116 B1 | 3/2012 |
| JP | 2012050817 A | 3/2012 |
| JP | 4948692 B2 | 6/2012 |
| KR | 20010062653 A | 7/2001 |
| KR | 100443600 B1 | 9/2004 |
| KR | 20060052161 A | 5/2006 |
| KR | 20070015215 A | 2/2007 |
| KR | 10-0702350 B1 | 4/2007 |
| KR | 101233733 B1 | 2/2013 |
| MX | 9702501 A | 4/1998 |
| MX | PA05010946 A | 4/2006 |
| NO | 311603 B1 | 12/2001 |
| NZ | 225382 A | 12/1996 |
| NZ | 236809 A | 12/1997 |
| NZ | 286537 A | 4/1998 |
| NZ | 521287 A | 8/2004 |
| RU | 2008 106 934 A | 10/2009 |
| RU | 2392970 C2 | 6/2010 |
| TW | 537906 B | 6/2003 |
| TW | I379695 B | 12/2012 |
| WO | 93/17726 A1 | 9/1993 |
| WO | 9641686 A1 | 12/1996 |
| WO | 9737692 A1 | 10/1997 |
| WO | 0038745 A1 | 7/2000 |
| WO | 0038746 A1 | 7/2000 |
| WO | 0158499 A1 | 8/2001 |
| WO | 02/41926 A1 | 5/2002 |
| WO | 02/43780 A1 | 6/2002 |
| WO | 2004/043499 A2 | 5/2004 |
| WO | 2005/011749 A2 | 2/2005 |
| WO | 2005118002 A2 | 12/2005 |
| WO | 2005118002 A3 | 8/2006 |
| WO | 2009058840 A1 | 5/2009 |
| WO | 2010/046891 A2 | 4/2010 |
| WO | 2011/041578 A2 | 4/2011 |
| WO | 2012/017720 A1 | 2/2012 |
| WO | 2012/037431 A1 | 3/2012 |
| WO | 2012/148589 A2 | 11/2012 |
| WO | 2012148589 A3 | 2/2013 |
| WO | 2016/010970 A1 | 1/2016 |
| WO | 2017/028980 A1 | 2/2017 |
| WO | 2017/043600 A1 | 3/2017 |
| WO | 2017/089258 A1 | 6/2017 |
| ZA | 9702844 B | 10/1998 |

OTHER PUBLICATIONS

Yuanyuan Xu et al., The Boom in 3D-Printed Sensor Technology, Sensors 2017; vol. 17, pp. 1-37.

Extended European Search Report for Application No. 18212574.0 dated Aug. 19, 2019, 15 Pages.

Russian Official Action and Search Report dated Jul. 1, 2019 for Aplication No. 2018128975, English Translation.

* cited by examiner

FLOW RESTRICTOR

FIELD

The subject matter disclosed herein relates to dry boosters, which are devices that assist in sterilizing medical devices having lumens, e.g., endoscopes.

BACKGROUND

Medical devices are typically sterilized before use in order to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO).

Certain sterilization techniques are conducted at pressures other than ambient pressure or atmospheric pressure. For example, the STERRAD® System, STERRAD® NX System or STERRAD® 100NX System of Advanced Sterilization Products, Division of Ethicon US, LLC, a Johnson & Johnson company, are examples of sterilization systems, or sterilizers, that vaporize hydrogen peroxide and operate at low pressures, e.g., less than 200 millitorr.

Various elongate medical devices having lumens, e.g., endoscopes, are challenging to sterilize for various reasons. For example, because pressure within a lumen decreases from the lumen's inlet as a function of length and diameter, the pressure drop must be overcome to ensure that sterilant passes through the entire lumen and reaches all surfaces of the lumen. Further, lumens may collect debris or be blocked by fluids, such as rinse water.

A dry booster is a device that may be connected to a lumen of an elongate medical device. When subject to a sterilization process in which pressure changes are implemented, pressure differentials between the inside of a dry booster at one end of the lumen and a pressure chamber at the other end of a lumen help pass a sterilant through the lumen, which assists in sterilizing the lumen.

SUMMARY

An apparatus that assists in sterilizing an endoscope inside a sterilizer employing a gaseous sterilant, e.g., hydrogen peroxide, is disclosed. The apparatus may include a dry booster and a flow restrictor. The flow restrictor may include a first tube having a first tube inlet, a first tube outlet, a first tube length, and a first tube radius. The flow restrictor may also include a second tube having a second tube inlet, a second tube outlet, a second tube length, and a second tube radius. The first tube outlet and second tube outlet may be connected to the dry booster. The first tube inlet may be connectable, directly or indirectly, to a first lumen of an endoscope. Similarly, the second tube inlet may be connectable, directly or indirectly, to a second lumen of an endoscope.

In some embodiments, the first tube length may be between approximately 10 mm and 20 mm, the first tube radius may be between approximately 2.5 mm and 9 mm, the second tube radius may be between approximately 0.25 mm and approximately 1 mm, and the second tube length may be between approximately 20 mm and approximately 5000 mm. For example, the first tube length may be approximately 20 mm, the first tube radius may be approximately 6 mm, the second tube radius may be approximately 0.25 mm and the second tube length may be approximately 20 mm.

In some embodiments, the apparatus further includes a spool that the second tube may be wrapped around. An adapter may also be included to assist in connecting the first tube outlet and the second tube outlet to the dry booster. That is, the first tube outlet and the second tube outlet may be connected to the adapter, and the adapter may be connected to the dry booster.

A method of sterilizing the endoscope using the apparatus is also disclosed. The method may include the following steps. A dry booster and a flow restrictor having a first end and a second end may be provided. An endoscope may also be provided. The endoscope may have a first lumen and a second lumen disposed therethrough. The first lumen may have a first radius and the second lumen may have a second radius that is at least twice as long as the first radius. The first end of the flow restrictor may be connected to the endoscope and the second end of the flow restrictor may be connected to the dry booster. The endoscope connected to the dry booster and the flow restrictor may be placed into a vacuum chamber of a sterilizer that employs a gaseous sterilant, such as hydrogen peroxide. The vacuum chamber may be closed. The endoscope connected to the dry booster and the flow restrictor may be subjected to a sterilization cycle including a gaseous sterilant. Sterilant may flow through the first lumen at a first flow rate. Sterilant may also flow through the second lumen at a second flow rate. The flow through the first lumen may be between plus or minus 25% of the flow rate through the second lumen. Alternatively, the first flow rate and the second flow rate may be equal.

In some variations of the method, the endoscope may be placed into a sterilization pouch before placing it into the vacuum chamber. Alternatively, the endoscope may be disposed in a sterilization tray before placing it into the vacuum chamber.

Also disclosed herein is a method of fabricating a flow restrictor. A first tube and a second tube may be provided. The first tube may have a first length and a first radius and the second tube may have a second length and a second radius that is less than the first radius. The first tube may be connected to a first endoscope lumen. The second tube may be connected to a second endoscope lumen that has a greater volume than the first endoscope lumen. The first tube and the second tube may be connected to a source of gas or liquid. A first flow rate through the first tube and a second flow rate through the second tube may be determined. The first flow rate may be compared to the second flow rate to determine whether the first flow rate is greater than the second flow rate. The second length may be adjusted to change the second flow rate.

In those cases where second flow rate is greater than the first flow rate, the second length may be adjusted by replacing the second tube with a third tube that is longer than the second tube. In those cases where the second flow rate is less than the first flow rate, the second length may be adjusted by removing a segment of the second tube, e.g., by cutting off the segment. The second tube may be wrapped onto a spool to assist in handling the flow restrictor.

BRIEF DESCRIPTION OF THE DRAWINGS

While the specification concludes with claims that particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Dry boosters may be used to help draw chemical sterilants into a lumen of an elongate medical device, e.g., an endoscope. Dry boosters are disclosed in U.S. Pat. Nos. 6,451,255 and 7,229,591, which are hereby incorporated by reference in their entirety. A dry booster may include an adapter to assist in establishing a connection between the dry booster and a lumen of an elongate medical device. An exemplary adapter is described in U.S. Pat. No. 6,187,265, which is hereby incorporated by reference in its entirety.

Figure 1:
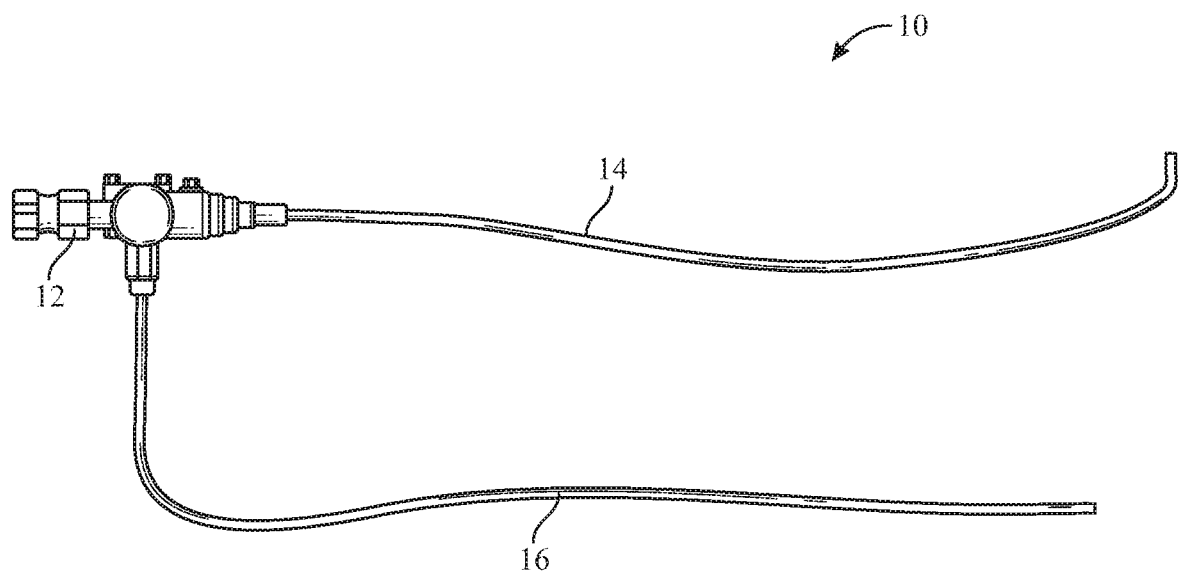
FIG. 1 depicts an endoscope.

FIG. 1 shows an exemplary endoscope, endoscope 10, which includes a body 12, an insertion tube 14, and an umbilical tube 16. Insertion tube 14 is the portion of the endoscope that may be inserted into a subject. Insertion tubes typically have a length of between approximately one foot and approximately seven feet. An insertion tube of an endoscope may include various channels (e.g., lumens) having different diameters ranging from approximately 1 mm to 10 mm. Some endoscopes include one or more channels for introducing, e.g., air, water, or a medical instrument therethrough. An instrument channel may have a diameter between approximately 3 mm and 8 mm, a water-nozzle channel may have a diameter between approximately 1 mm and 6 mm, a water-jet nozzle channel may have a diameter between approximately 1 mm and 6 mm, and an air-nozzle channel may have a diameter between approximately 1 mm and 6 mm. These channels must be decontaminated between uses, e.g., by sterilization.

During sterilization of an endoscope connected to a dry booster, a sterilant is typically introduced into a sterilizer's vacuum chamber under conditions whereby the pressure in the vacuum chamber is greater than the pressure in the dry booster. Thus, the dry booster provides a suction force that helps the sterilant flow through the channels of the endoscope. When a multi-lumen endoscope is connected to a dry booster for decontamination by a low pressure sterilization cycle, challenges arise concerning providing a sufficient amount of sterilant through the smaller diameter channels. Specifically, the smaller diameter channels provide a greater resistance to a sterilant's flow than the larger diameter channels. Accordingly, excess sterilant may flow through the larger channels while an inadequate volume may flow through the smaller diameter channels. In other words, when the difference in the resistance between a large channel and a small channel is great, the sterilant will "prefer" to flow through a larger channel instead of a small channel.

After recognizing this problem, the inventor conceived of using flow restrictors to increase the resistance to flow provided by the larger channels in order to even the flow of sterilant through the channels to increase the likelihood that a sufficient volume of sterilant flows through each channel.

Figure 2:
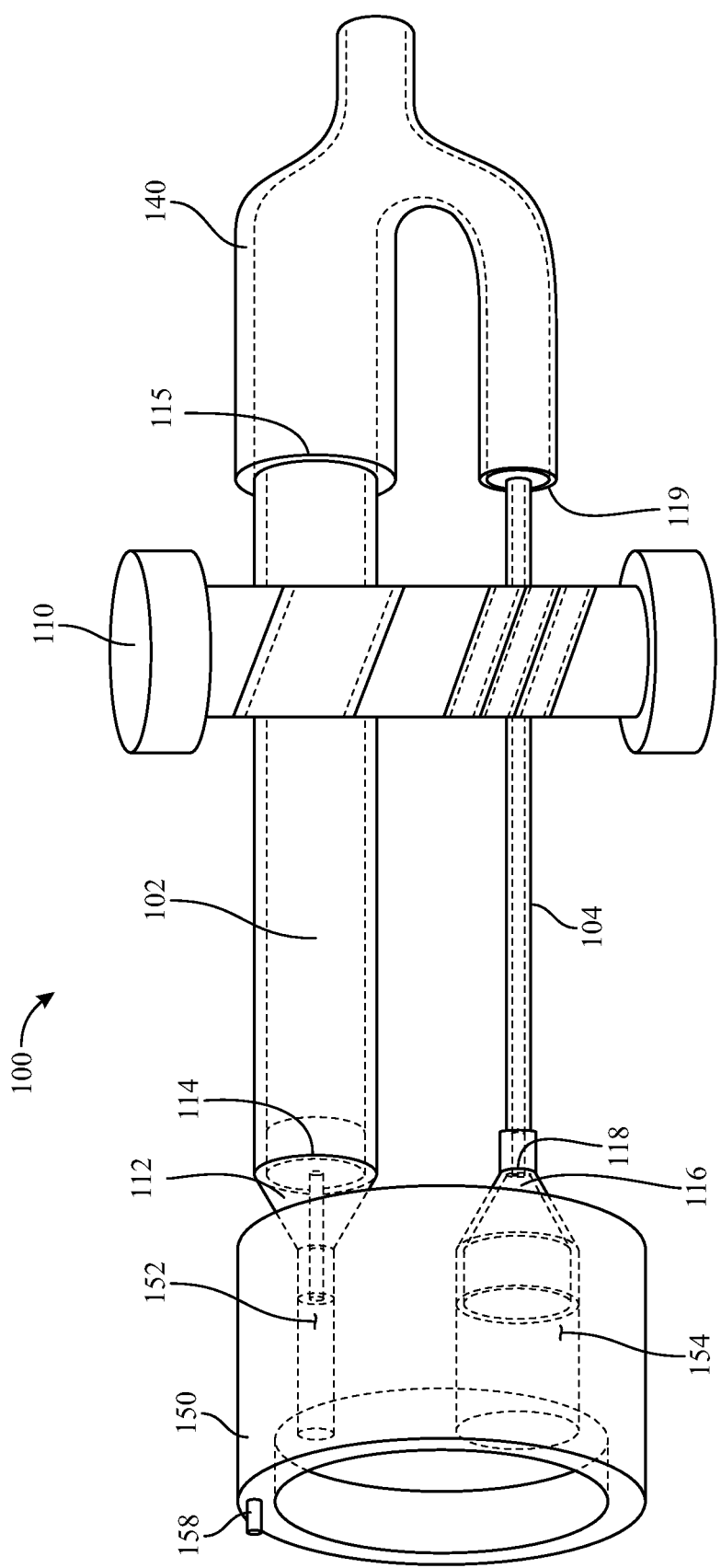
FIG. 2 depicts a flow restrictor.

FIG. 2 shows a flow restrictor 100 that may be used to even the flow of a sterilant through multiple lumens of an endoscope connected to a dry booster. Flow restrictor 100 includes a first tube 102 and a second tube 104. In certain embodiments, flow restrictor 100 may include a spool 110 about which at least second tube 104 may be wrapped, a first tube connector or adapter 112, a second tube connector or adapter 116, a dry-booster adapter 140 and an endoscope adapter 150. Spool 110 may be considered optional for tubing management. However, alternate forms of tubing management may be implemented. For example, second tube 104 may be formed by heat treatment using a mandrel to a convenient form, such as a coiled configuration. First tube connector or adapter 112 may be configured to mate first tube 102 to a first channel of an endoscope or a first channel 152 of endoscope adapter 150. First adapter 112 may be connected to a first end 114 of first tube 102. Second tube connector or adapter 116 may be configured to mate second tube 104 to a second channel of an endoscope or to a second channel 154 of endoscope adapter 150. Second adapter 116 may be connected to a first end 118 of second tube 104. In some embodiments, dry-booster adapter 140 may be connected to second end 115 of first tube 102 and to second end 119 of second tube 104 in order to mate tubes 102 and 104 to a dry booster (e.g., dry booster 30, FIG. 4).

Figure 3:
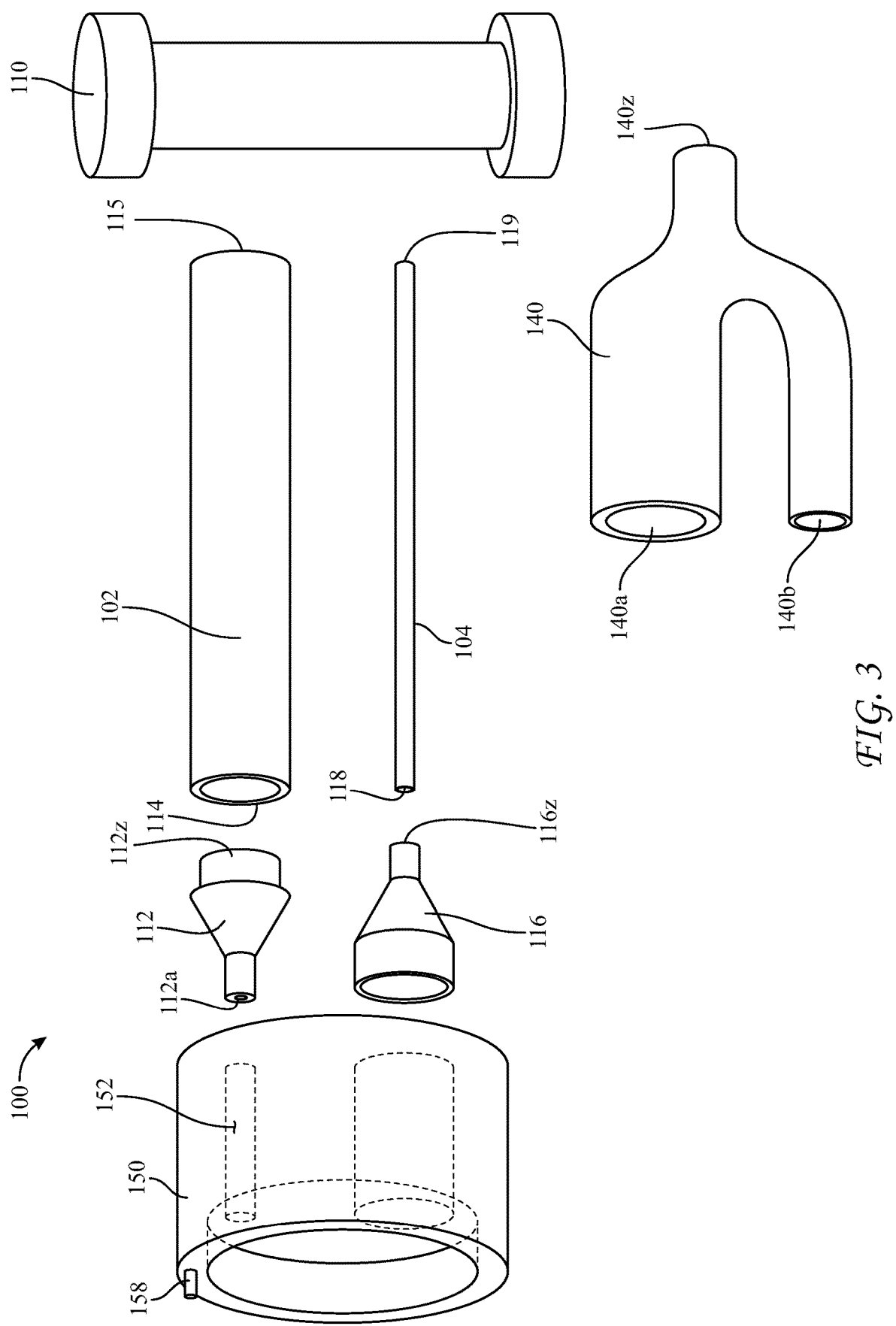
FIG. 3 depicts an exploded view of the flow restrictor of FIG. 2.

FIG. 3 reflects an exploded view of flow restrictor 100. Whereas first adapter 112 includes a single inlet 112a and a single outlet 112z and whereas second adapter 116 includes a single inlet 116a and a single outlet 116z, dry-booster adapter 140 includes two inlets—first inlet 140a and second inlet 140b—and a single outlet 140z. Dry-booster adapter 140 may facilitate connecting flow restrictor 100 to a dry booster. However, dry-booster adapter 140 need not be used such that first tube 102 and second tube 104 may be individually and separately connected to a dry booster. In various embodiments, dry-booster 140 may be manufactured by 3D printing, injection molding, or dip molding.

Channels 152 and 154 of endoscope adapter 150 may be aligned with channels of an endoscope and have greater diameters, from approximately 2 mm to 20 mm, than endoscope channels, which are on the order of approximately 1 mm to 10 mm. To help ensure that channels 152 and 154 properly align with the endoscope's channels, endoscope adapter 150 may further include any of various alignment features. For example, small projections on a surface of endoscope adapter 150 may mate with endoscope channels, including those to which channels 152 and 154 align, or other features of an endoscope that are specifically designed to mate with an alignment feature. For example, a short cylindrical projection 158 on a surface of endoscope adapter 150 may mate with a short cylindrical cut-out on the tip of the endoscope. Accordingly, connection of first tube 102 and second tube 104 to endoscope channels may be facilitated via an indirect connection using endoscope adapter 150—and connecting first tube 102 to channel 152 and second tube 104 to channel 154—as compared to connecting first tube 102 and second tube 104 directly to endoscope channels. However, endoscope adapter 150 is optional. A direct connection of first tube 102 and second tube 104 to channels of an endoscope may be made if the sizing of the tubes and channels permits.

Figure 4:
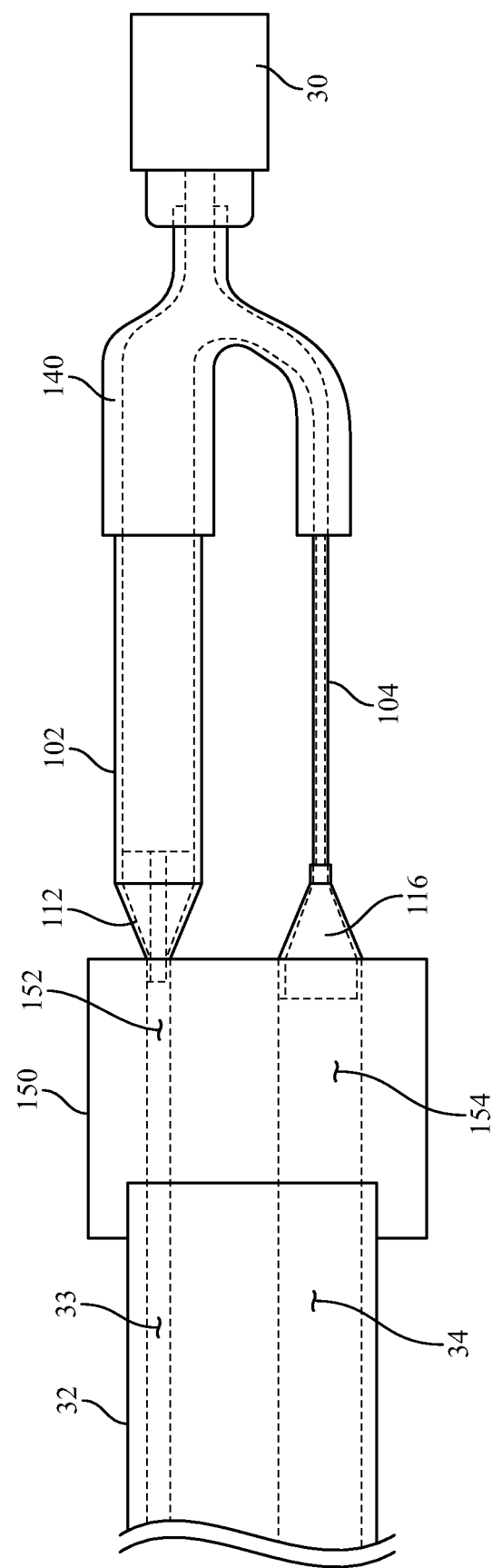
FIG. 4 depicts the flow restrictor of FIG. 2 connected an endoscope and a dry booster.

FIG. 4 shows flow restrictor 100 connected on one end to a dry booster 30 and on the other end to a two-channel insertion tube 32 of an endoscope having a first channel 33 and a second channel 34 that has a diameter larger than the diameter of first channel 33. As shown, first tube 102 connects to first channel 33 and second tube 104 connects to second channel 34 via endoscope adapter 150 including channels 152 and 154. As shown, dry booster 30 is connected to a distal end of insertion tube 32. In some embodiments, however, dry booster 30 may also be connected closer to a proximal end of insertion tube 32, e.g., via ports on the endoscope's control body.

The lengths and inner diameters (and correspondingly, outer diameters) of first tube 102 and second tube 104 depend upon and are determined in reference to the restriction in flow provided by channels 33 and 34. Flow through each of channels 33 and 34 may be approximated by the Hagen-Poiseuille equation:

$$\Delta P = \frac{8\mu L Q}{\pi R^4},$$

where $\Delta P$ is the change in pressure in the channel, $\mu$ is the viscosity of the fluid, L is the length of the channel, Q is the volume flow rate of the channel, and R is the radius of the channel. The Hagen-Poiseuille equation provides that a drop in pressure of a fluid flowing through a long pipe of uniform cross section is proportional to the length of the pipe and inversely proportional to the radius to the fourth power. This information can be used to determine dimensions for first tube 102 and second tube 104.

In some embodiments, first tube 102 may have the same length and diameter as second channel 34 and second tube 104 may have the same length and diameter as first channel 33. Thus, a first conduit formed by first tube 102 and second channel 34 would be a "reflection" of a second conduit formed by second tube 104 and first channel 33. Accordingly, in these embodiments, proximate dry booster 30 (e.g., just before the inlets 140a and 140b of dry-booster adapter 140), a pressure in first tube 102 should approximate or be equal to a pressure in second tube 104, indicating that the flow of sterilant through each conduit should be similar.

In other embodiments, the dimensions of first tube 102 (which is connected to smaller channel 33) may be chosen so that first tube 102 does not provide further restriction to the flow. Thus, the pressure at the outlet of channel 33 would be equal or approximately equal to pressure at the outlet of tube 102. For example, the radius of first tube 102 should be chosen equal to or larger (e.g., approximately 1.5× to 3×) the radius of the endoscope's largest channel, which, in the present example, would be second channel 34. As per the dimensions specified set forth above concerning endoscope channels, this suggests that the radius of first tube 102 should be between approximately 2.5 mm and 9 mm. For example, the radius of first tube 102 may be approximately 6 mm. Further, the length of first tube 102 should be short, e.g., from about approximately 10 mm to about approximately 100 mm. For example, the length of first tube 102 may be approximately 20 mm. If design considerations suggest that first tube 102 may be longer, first tube 102 may be longer than approximately 100 mm because the pressure drop depends more heavily on radius than length.

Second tube 104 should be designed to restrict the flow of sterilant passing through channel 34 such that the flow therethrough approximates the flow through channel 33. That is, the flow through channel 34 may be between plus or minus 25% of the flow rate through channel 33. This may be accomplished by choosing dimensions of second tube 104 that result in a pressure at the outlet of second tube 104 that approximates or is equal the pressure at the outlet of channel 33.

The following design equation may be used to aid in determining dimensions of second tube 104:

$$\frac{L_{tube2}}{R_{tube2}^4} = L_{WL}\left(\frac{1}{R_{chan1}^4} - \frac{1}{R_{chan2}^4}\right),$$

where $L_{tube2}$ is the length of second tube 102, $R_{tube2}$ is the radius of second tube 102, LWL is the working length of insertion tube 32. $R_{chan1}$ is the radius of smaller channel 33 and $R_{chan2}$ is the radius of larger channel 34. This equation is derived from the Hagen-Poiseuille equation and based on the following three assumptions. First, if the pressure at the outlet of tube 102 and tube 104 are equal or approximately equal, then the overall flow rate through the first conduit should be equal or approximately equal to the flow rate through the second conduit. Second, the pressure at the outlet of second tube 104 should be approximately equal to the pressure at the outlet of first channel 33. Third, the lengths of first channel 33 and second channel 34 are equal to the working length of insertion tube 32.

For example, consider an endoscope that has an insertion tube 32 working length of 2000 mm, a first channel 33 (e.g., water jet nozzle) that has a radius of 1.25 mm, and a second channel 34 (e.g., instrument channel) that has a radius of 3 mm. Also consider that rubber tubing having an internal diameter of may be purchased having an internal radius of between 0.25 mm and 1 mm. Setting $R_{tube2}$ as equal to 0.25 mm, the design equation indicates that $L_{tube2}$ should be approximately 20 mm. Accordingly, flow restrictor 100 may be designed to even the flow through channels 33 and 34 by specifying that first tube 102 has a radius between approximately 3 mm and approximately 6 mm, e.g., 3 mm, first tube 102 has a length between approximately 10 mm and 20 mm, e.g., 20 mm, second tube 104 has a radius of approximately 0.25 mm, and second tube 104 has a length off approximately 20 mm. So specified, flow restrictor 100 need not include a spool (e.g., 106) for managing the tubes because tubes that are 20 mm or less are manageable and not easily tangled.

Next consider this same example, but that $R_{tube2}$ is set to be 1 mm. In that case, the design equation indicates that $L_{tube2}$ should be approximately 5028 mm. So specified, flow restrictor 100 likely should include a spool for managing at least tube 2 because a 5000 mm tube may otherwise be difficult to manage.

The design equation may also be used to determine the dimensions of tubes in flow restrictors having greater than two tubes that are intended to be used upon endoscopes having more than two channels. As with the two-channel restrictor, the tube that is to be connected to the smallest channel should provide little or no additional restriction to flow. Accordingly, it should have a radius equal to or larger (e.g., approximately 1.5× to 3×) than the radius of the endoscope's largest channel and a length from about approximately 10 mm to about approximately 100 mm. The design equation may be used to determine the dimensions of all other tubes of the flow restrictor (i.e., all tubes that are not connected to the smallest channel of the endoscope) because the design equation is independent of variables concerning other tubes and channels except for the radius of the smallest channel. Thus, it may be convenient to express the design equation more generally as $$\frac{L_{tubei}}{R_{tubei}^4} = L_{WL}\left(\frac{1}{R_{chan1}^4} - \frac{1}{R_{chani}^4}\right),$$

where i is an index equaling 2, 3, 4, or up to the number of channels the endoscope has that should receive sterilant during a sterilization procedure. So, for example, for a flow restrictor being connected to an endoscope that has four channels, i would equal 3 for the third tube and i would equal 4 for the fourth tube.

In practice, the flow rates of a sterilant through an endoscope's channels may approximate each other when a flow restrictor is attached to the endoscope; however, the flow rates not be equal to each other for various reasons. For example, the Hagen-Poiseuille equation is based on a constant radius, but, referring to flow restrictor 100, the internal radius of tube 104 may not be constant along its length due to manufacturing imperfections. To increase the likelihood of fabricating a flow restrictor 100 that may enable equal or nearly equal flow rates through an endoscope's channels, the flow rate through tubes 102 and 104 of flow restrictor 100 may be measured or observed. Should they be different, the length of tube 104 may be adjusted. For example, tubes 102 and 104 may be designed as described above using the design equation and connected to insertion tube 32. However before connecting tubes 102 and 104 to dry booster 30 and/or dry-booster adapter 140, a gas (e.g., air) or liquid (e.g. water) source may be connected to tubes 102 and 104, either at a control body of insertion tube 32 or at the open ends of tubes 102 and 104. The flow of the water or gas through tubes 102 and 104 may be measured (e.g., using a flow meter) and/or observed (e.g., by collecting water in a vessel, such as a graduated cylinder). If the flow through tube 104 is faster than the flow through tube 102, tube 104 may be elongated or have its radius reduced (e.g., by replacing tube 104 with a longer piece of tubing or piece of tubing having a smaller radius). If the flow through tube 104 is slower than the flow through tube 102, tube 104 may be shortened or have its radius enlarged (e.g., by cutting off a portion of tube 104 or replacing tube 104 with a piece of tubing have a larger radius). In this manner the flow rate through tube 104 may be fine tuned until it is equal or nearly equal to the flow rate through tube 102.

Flow restrictor 100 may be used to assist in sterilizing an elongate medical device, such as an endoscope, having at least a first lumen and a second lumen disposed therethrough, the first lumen having a first radius and the second lumen having a second radius that is at least twice as long as the first radius. First, the elongate medical device, flow restrictor, and a dry booster may be provided. Second, the dry booster may be connected to a first end of the flow restrictor. Third, the endoscope may be connected to a second end of the flow restrictor. Fourth the endoscope connected to the dry booster and the flow restrictor may be placed into a vacuum chamber of a sterilizer. In some variations of this method, the endoscope may be disposed within a sterilization tray or a sterilization pouch before it is placed into the vacuum chamber. Fourth, the vacuum chamber may be closed. Fifth, the endoscope may be subject to a sterilization cycle that includes a gaseous sterilant, such as hydrogen peroxide. Sixth, sterilant may flow through the first lumen at a first flow rate and the sterilant may flow through the second lumen at a second flow rate. The first flow rate and the second flow rate may be approximately equal. That is, the flow through channel 34 may be between plus or minus 25% of the flow rate through channel 33. In certain variations of the method, the first flow rate and the second flow rate may be equal.

Flow restrictor 100 may be fabricated according to the following procedure. First, a length of first tube 102 and a second tube 104 are determined with reference to the design equation. Second, first tube 102 is connected to endoscope channel 33 and second tube 104 is connected to endoscope channel 34. Third, a first flow-rate though first tube 102 is determined and a second flow-rate through second tube 104 is determined. Fourth, the first-flow rate is compared to the second flow rate. Fifth, the second flow rate is determined to be equal to the first flow rate, less than the first flow rate, or more than the first flow rate. Sixth, if the first flow rate is less than the second flow rate, second tube 104 may be elongated by using a longer piece of tubing for second tube 104. That is, second tube 104 may be replaced by a third tube that is longer than second tube 104. Seventh, if the first flow great is greater than the second flow rate, second tube 104 may be shorted by removing a segment therefrom, e.g., by cutting off a portion of second tube 104 using a scissors. Eighth, second tube 104 may be wrapped onto a spool. Ninth, first tube 102 may be wrapped onto the spool.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:
1. An apparatus, comprising:
   a dry booster; and
   a flow restrictor including
      a first tube having a first tube inlet, a first tube outlet, a first tube length, and a first tube radius, and
      a second tube having a second tube inlet, a second tube outlet, a second tube length, and a second tube radius;
      wherein the first tube outlet and second tube outlet are connected to the dry booster, such that a fluid that is flowed through the flow restrictor flows separately through the first tube and the second tube.
2. The apparatus of claim 1, wherein the first tube inlet is connectable directly or indirectly to a first lumen of an endoscope and the second tube inlet is connectable directly or indirectly to a second lumen of an endoscope.
3. The apparatus of claim 2, wherein the first tube length is between approximately 10 mm and 20 mm.
4. The apparatus of claim 3, wherein the first tube radius is between approximately 2.5 mm and 9 mm.
5. The apparatus of claim 4, wherein the second tube radius is between approximately 0.25 mm and approximately 1 mm.
6. The apparatus of claim 5, wherein the second tube length is between approximately 20 mm and approximately 5000 mm.
7. The apparatus of claim 6, wherein the first tube length is approximately 20 mm and the first tube radius is approximately 6 mm.

8. The apparatus of claim 7, wherein the second tube radius is approximately 0.25 mm and the second tube length is approximately 20 mm.

9. The apparatus of claim 1, further comprising a spool wherein at least the second tube is wrapped around the spool.

10. The apparatus of claim 9, further comprising an adapter, wherein first tube outlet and second tube outlet are connected to the dry booster via the adapter.

\* \* \* \* \*